(12) United States Patent
Kuboi et al.

(10) Patent No.: US 12,704,245 B2
(45) Date of Patent: Aug. 11, 2026

(54) LIGHT SOURCE DEVICE AND COOLING METHOD

(71) Applicant: OLYMPUS MEDICAL SYSTEMS CORP., Tokyo (JP)

(72) Inventors: Toru Kuboi, Machida (JP); Yusuke Yabe, Chofu (JP); Shuichi Kudo, Kawasaki (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 7 days.

(21) Appl. No.: 18/922,809

(22) Filed: Oct. 22, 2024

(65) Prior Publication Data

US 2025/0137635 A1 May 1, 2025

Related U.S. Application Data

(60) Provisional application No. 63/545,621, filed on Oct. 25, 2023.

(51) Int. Cl.

| | |
|---|---|
| ***F21V 29/71*** | (2015.01) |
| ***A61B 1/06*** | (2006.01) |
| ***F21V 29/60*** | (2015.01) |
| ***F21V 29/76*** | (2015.01) |
| ***F21V 33/00*** | (2006.01) |

(52) U.S. Cl.

CPC .......... *F21V 29/717* (2015.01); *A61B 1/0661* (2013.01); *F21V 29/60* (2015.01); *F21V 29/767* (2015.01); *F21V 33/0068* (2013.01)

(58) Field of Classification Search

CPC ................. F21V 29/717; F21V 29/503; F21V 29/51–59; F21V 29/70–83

See application file for complete search history.

(56) References Cited

U.S. PATENT DOCUMENTS

2020/0379247 A1* 12/2020 Pascale ............... F28D 15/0275

FOREIGN PATENT DOCUMENTS

| | | |
|---|---|---|
| JP | 2000104951 A | 4/2000 |
| JP | 2004184613 A | 7/2004 |
| JP | 2008158191 A | 7/2008 |
| JP | 2019136555 A | 8/2019 |

* cited by examiner

*Primary Examiner* — Sean P Gramling

(74) *Attorney, Agent, or Firm* — Scully, Scott, Murphy & Presser, P.C.

(57) ABSTRACT

A light source device includes: a first light emitting element; a second light emitting element; and a heat sink configured to dissipate heat of the first light emitting element and heat of the second light emitting element. The heat sink includes: a first heat dissipation portion that is disposed on a flow path of a fluid, the first heat dissipation portion being configured to radiate the heat of the first light emitting element and the heat of the second light emitting element to the fluid; and a second heat dissipation portion that is disposed on the flow path, the second heat dissipation portion being configured to radiate the heat of the second light emitting element to the fluid.

20 Claims, 17 Drawing Sheets

FIG.1

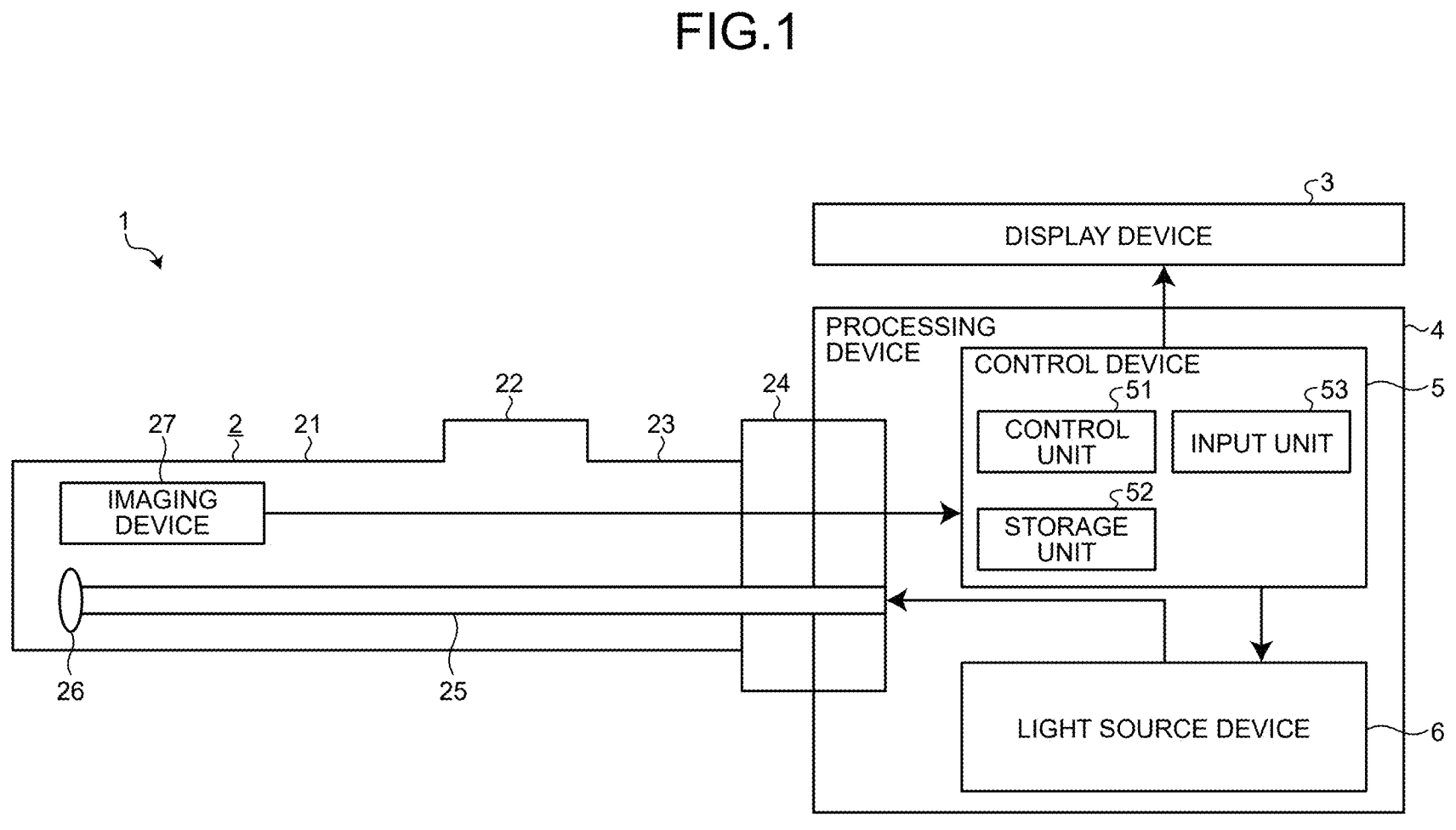

DISPLAY DEVICE
PROCESSING DEVICE
CONTROL DEVICE
CONTROL UNIT
STORAGE UNIT
INPUT UNIT
LIGHT SOURCE DEVICE
IMAGING DEVICE
1
2
3
4
5
6
21
22
23
24
25
26
27
51
52
53

FRONT SIDE
BACK SIDE
25
651
652
65
6
7
624
631
632
633
621
611
811(8)
812(8)
813(8)
622
623
613
612
+X
+Y
+Z 123
61
61B1
122
11
123
12
SC
81
A

LIGHT SOURCE DEVICE AND COOLING METHOD

CROSS-REFERENCE TO RELATED APPLICATION

This application is based on and claims priority under 35 U.S.C. § 119 to U.S. Provisional Application No. 63/545,621, filed Oct. 25, 2023, the entire contents of which are incorporated herein by reference.

BACKGROUND

1. Technical Field

The present disclosure relates to a light source device and a cooling method.

2. Related Art

In the related art, a light source device including a plurality of light emitting elements is known (see, for example, JP 2008-158191 A).

In the light source device described in Patent Literature 1, in order to collectively cool the plurality of light emitting elements, the plurality of light emitting elements are thermally connected to the same heat dissipation portion (cooling unit).

SUMMARY

In some embodiments, a light source device includes: a first light emitting element; a second light emitting element; and a heat sink configured to dissipate heat of the first light emitting element and heat of the second light emitting element. The heat sink includes: a first heat dissipation portion that is disposed on a flow path of a fluid, the first heat dissipation portion being configured to radiate the heat of the first light emitting element and the heat of the second light emitting element to the fluid; and a second heat dissipation portion that is disposed on the flow path, the second heat dissipation portion being configured to radiate the heat of the second light emitting element to the fluid, and an allowable thermal resistance for the heat sink in the first light emitting element calculated from a difference between a maximum junction temperature and an ambient temperature and a heat generation amount of the first light emitting element is higher than an allowable thermal resistance for the heat sink in the second light emitting element calculated from a difference between a maximum junction temperature and an ambient temperature and a heat generation amount of the second light emitting element.

In some embodiments, provided is a method of cooling a first light emitting element and a second light emitting element thermally connected to a heat sink that includes a first heat dissipation portion and a second heat dissipation portion. The method includes: making an allowable thermal resistance for the heat sink in the first light emitting element calculated from a difference between a maximum junction temperature and an ambient temperature and a heat generation amount of the first light emitting element higher than an allowable thermal resistance for the heat sink in the second light emitting element calculated from a difference between a maximum junction temperature and an ambient temperature and a heat generation amount of the second light emitting element; dissipating heat of the first light emitting element and heat of the second light emitting element to the first heat dissipation portion disposed on a flow path of a fluid; and dissipating the heat of the second light emitting element to the second heat dissipation portion disposed on the flow path of the fluid.

In some embodiments, a light source device includes: a first light emitting element; a second light emitting element; and a heat sink that dissipates heat of the first light emitting element and heat of the second light emitting element. The heat sink includes: a first heat dissipation portion that is disposed on a flow path of a fluid, the first heat dissipation portion being configured to dissipate the heat of the first light emitting element and the heat of the second light emitting element to the fluid; a second heat dissipation portion that is disposed on the flow path, the second heat dissipation portion being configured to dissipate the heat of the second light emitting element to the fluid; a first heat pipe configured to thermally connect the first light emitting element and the first heat dissipation portion; and a second heat pipe configured to thermally connect the second light emitting element, and the first heat dissipation portion and the second heat dissipation portion.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 1 is a diagram illustrating a configuration of an endoscope system according to a first embodiment.

DETAILED DESCRIPTION

Figure 2:
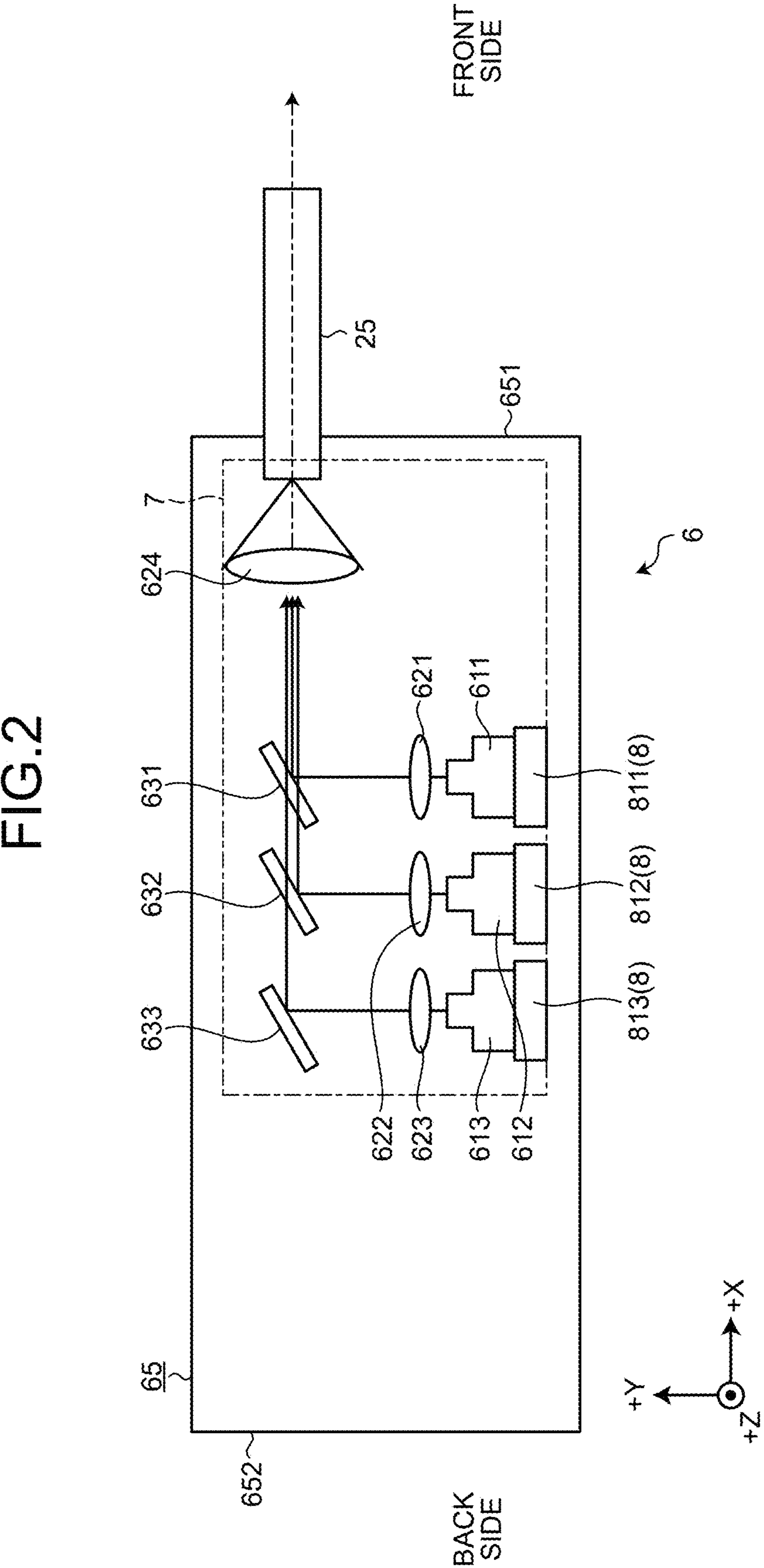
FIG. 2 is a view illustrating an internal configuration of a light source device.

Hereinafter, embodiments for carrying out the present invention (hereinafter, referred to as the embodiments) will be described with reference to the drawings. Note that the present invention is not limited to the embodiments described below. Further, in the description of the drawings, the same reference signs denote the same parts.

First Embodiment

Configuration of Endoscope System

FIG. 1 is a diagram illustrating a configuration of an endoscope system 1 according to a first embodiment.

The endoscope system 1 is a system that is used in a medical field and observes the inside of a subject (the inside of a living body). As illustrated in FIG. 1, the endoscope system 1 includes an endoscope 2, a display device 3, and a processing device 4.

In the first embodiment, the endoscope 2 is a so-called flexible endoscope. The endoscope 2 is partially inserted into a living body, images the inside of the living body, and outputs an image signal generated by the imaging. Then, as illustrated in FIG. 1, the endoscope 2 includes an insertion unit 21, an operating unit 22, a universal cord 23, and a connector unit 24.

The insertion unit 21 is a portion at least a part of which has flexibility and is inserted into the living body. As illustrated in FIG. 1, a light guide 25, an illumination lens 26, and an imaging device 27 are provided in the insertion unit 21.

The light guide 25 is routed from the insertion unit 21 to the connector unit 24 through the operating unit 22 and the universal cord 23. One end of the light guide 25 is positioned at a distal end portion in the insertion unit 21. In addition, in a state where the endoscope 2 is connected to the processing device 4, the other end of the light guide 25 is positioned in the processing device 4. Then, the light guide 25 transmits light supplied from a light source device 6 in the processing device 4 from the other end to the one end.

The illumination lens 26 faces the one end of the light guide 25 in the insertion unit 21. Then, the illumination lens 26 irradiates the inside of the living body with the light transmitted by the light guide 25.

The imaging device 27 is provided at the distal end portion in the insertion unit 21. Then, the imaging device 27 includes an imaging element such as a charge coupled device (CCD) or a complementary metal oxide semiconductor (CMOS) that receives a subject image from the inside of the living body and converts the subject image into an electric signal, and outputs an image signal generated by imaging.

The operating unit 22 is connected to a proximal end portion in the insertion unit 21. Then, the operating unit 22 receives various operations on the endoscope 2.

The universal cord 23 extends from the operating unit 22 in a direction different from a direction in which the insertion unit 21 extends, and is a cord in which a signal line, the light guide 25, and the like that electrically connect the imaging device 27 and a control device 5 in the processing device 4 are disposed.

The connector unit 24 is provided at an end portion of the universal cord 23 and is detachably connected to the processing device 4.

The display device 3 is a liquid crystal display (LCD), an electro luminescence (EL) display, or the like, and displays an image or the like subjected to image processing by the processing device 4.

As illustrated in FIG. 1, the processing device 4 includes the control device 5 and the light source device 6. In the present embodiment, the light source device 6 and the control device 5 are provided in one casing as the processing device 4, but the embodiment is not limited thereto, and the light source device 6 and the control device 5 may be provided in separate casings.

The light source device 6 supplies illumination light to the other end of the light guide 25 under the control of the control device 5.

Note that a detailed configuration of the light source device 6 will be described in "Configuration of Light Source Device" described below.

The control device 5 integrally controls an operation of the entire endoscope system 1. Then, as illustrated in FIG. 1, the control device 5 includes a control unit 51, a storage unit 52, and an input unit 53.

The control unit 51 includes a controller such as a central processing unit (CPU) or a micro processing unit (MPU), or an integrated circuit such as an application specific integrated circuit (ASIC) or a field programmable gate array (FPGA), and controls an operation of the entire endoscope system 1.

The storage unit 52 stores various programs to be executed by the control unit 51, information necessary for processing in the control unit 51, and the like.

The input unit 53 is implemented using a keyboard, a mouse, a switch, a touch panel, or the like, and receives a user operation of a user such as an operator. Then, the input unit 53 outputs an operation signal corresponding to the user operation to the control unit 51.

Configuration of Light Source Device

Next, a configuration of the light source device 6 will be described.

FIG. 2 is a diagram illustrating an internal configuration of the light source device 6. In FIG. 2, a cooling unit 7 is indicated by a line with alternating long and short dashes for convenience of description.

As illustrated in FIG. 2, the light source device 6 includes red, green, and blue light sources 611 to 613, first to fourth lenses 621 to 624, first to third dichroic mirrors 631 to 633, the cooling unit 7, and a casing 65 in which these portions 611 to 613, 621 to 624, 631 to 633, and 7 are housed.

The red light source 611 includes a semiconductor light emitting element such as a light emitting diode (LED) or a laser diode (LD), and emits red light (for example, light in a wavelength band of about 600 to 700 nm). The red light source 611 corresponds to a first light emitting element, and a maximum junction temperature of the red light source 611 is a first temperature.

The blue light source 613 includes a semiconductor light emitting element such as an LED or an LD, and emits blue light (for example, light in a wavelength band of about 430 to 490 nm). A maximum junction temperature of the blue light source 613 is a second temperature higher than the first temperature.

The green light source 612 includes a semiconductor light emitting element such as an LED or an LD, and emits green light (for example, light in a wavelength band of about 490 to 550 nm). The green light source 612 corresponds to a second light emitting element, and a maximum junction temperature of the green light source 612 is a third temperature equal to or higher than the second temperature. That is, the red light source 611 has the maximum junction temperature lower than that of the green light source 612. The green light source 612 generates a larger amount of heat than the red light source 611.

The first to third dichroic mirrors 631 to 633 reflect rays of light from the red, green, and blue light sources 611 to 613 to cause the rays of light to travel on the same optical axis.

Specifically, the first dichroic mirror 631 reflects red light emitted from the red light source 611 and collected by the first lens 621, and transmits light in a wavelength band other than the red light.

The second dichroic mirror 632 reflects green light emitted from the green light source 612 and collected by the second lens 622, and transmits light in a wavelength band other than the green light.

The third dichroic mirror 633 reflects blue light emitted from the blue light source 613 and collected by the third lens 623, and transmits light in a wavelength band other than the blue light.

Then, the fourth lens 624 collects illumination light (white light) obtained by combining the red light, the green light, and the blue light, which have passed through the first to third dichroic mirrors 631 to 633, and guides the light to the other end of the light guide 25.

In the casing 65, a side wall 651 (FIG. 2) on a side to which the other end of the light guide 25 is connected is a side wall on a front side where a doctor or the like operating the endoscope 2 is present. A side wall 652 (FIG. 2) facing the side wall 651 is a side wall on a back side.

The cooling unit 7 dissipates heat generated in the red, green, and blue light sources 611 to 613.

A detailed configuration of the cooling unit 7 will be described in "Configuration of Cooling Unit" described below.

Configuration of Cooling Unit

Next, a configuration of the cooling unit 7 will be described.

Figure 3:
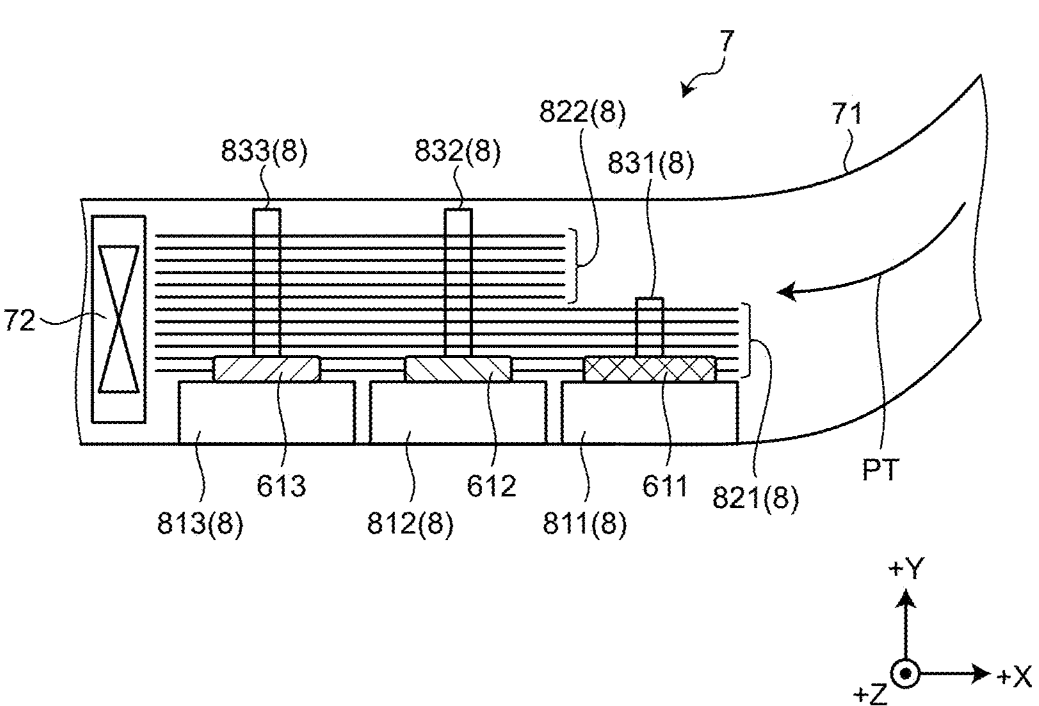
FIG. 3 is a view for describing a configuration of a cooling unit.
Figure 4:
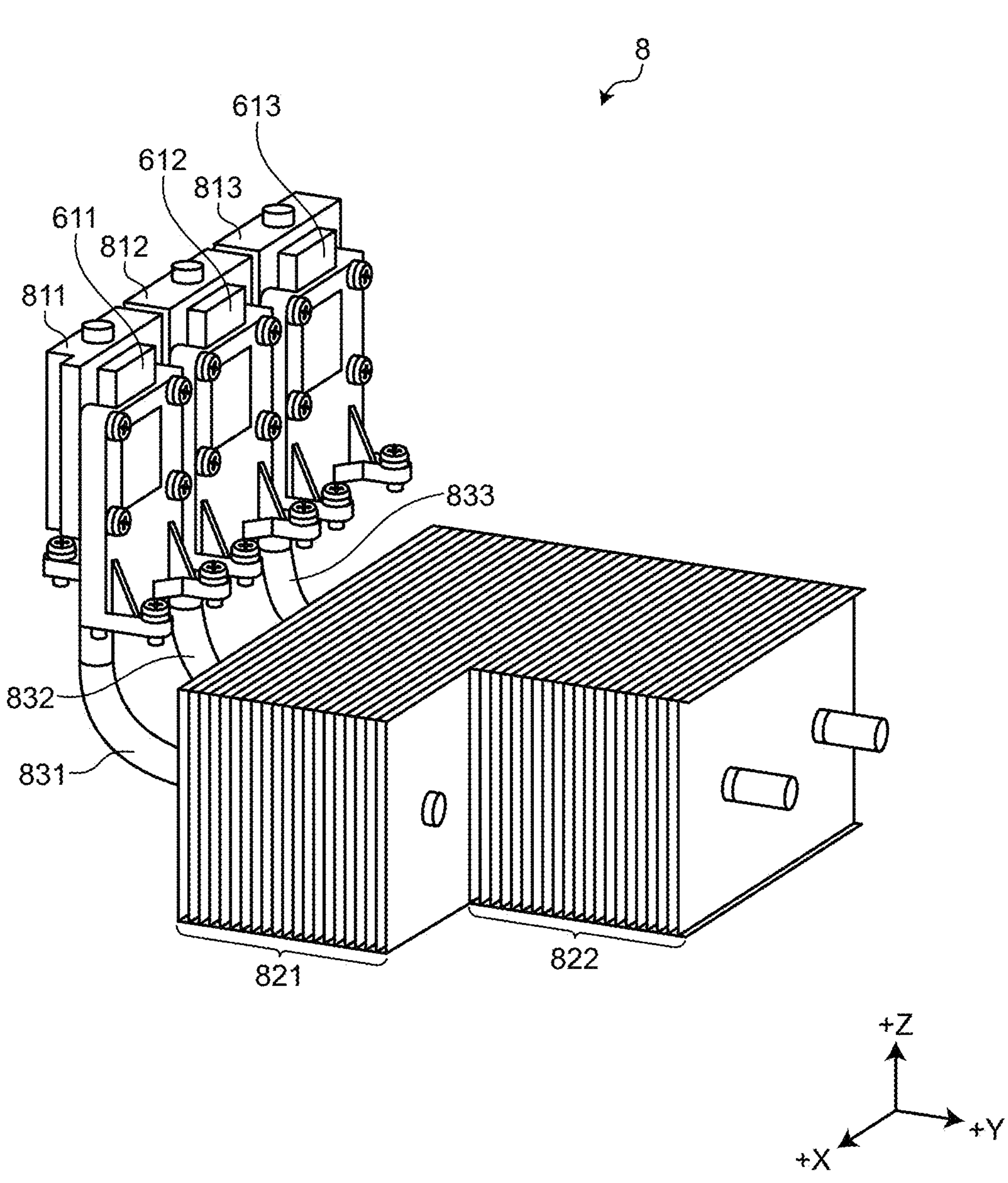
FIG. 4 is a view for describing a configuration of the cooling unit.

FIGS. 3 and 4 are views illustrating the configuration of the cooling unit 7. Specifically, FIG. 3 is a plan view illustrating an overall configuration of the cooling unit 7. FIG. 4 is a perspective view illustrating a configuration of a heat sink 8. In FIG. 3, a Z axis indicates an axis parallel to a vertical direction (a +Z axis direction is an upward direction). An X axis and a Y axis are two axes orthogonal to each other and orthogonal to the Z axis (a +X-axis direction is a direction from the side wall 652 on the back side toward the side wall 651 on the front side).

As illustrated in FIGS. 3 and 4, the cooling unit 7 includes a duct 71, a cooling fan 72, and the heat sink 8.

The duct 71 is disposed on a lower side (−Z-axis direction side) of the red, green, and blue light sources 611 to 613, the first to fourth lenses 621 to 624, and the first to third dichroic mirrors 631 to 633. One end side of the duct 71 communicates with an intake hole (not illustrated) formed in the side wall 651 on the front side (+X-axis side), and the other end side of the duct 71 communicates with an exhaust hole (not illustrated) formed in the side wall 652 on the back side (−X-axis side). The duct 71 forms a flow path PT (FIG. 3) through which air (fluid) flows from the intake hole toward the exhaust hole. As illustrated in FIG. 3, among the red, green, and blue light sources 611 to 613, the red light source 611 is disposed at a position upstream (on a +X-axis side) on the flow path PT. The blue light source 613 is disposed at a position downstream (on a −X-axis side) on the flow path PT, and the green light source 612 is disposed between the red light source 611 and the blue light source 613.

The cooling fan 72 is disposed to face the exhaust hole, and forcibly circulates the air from the intake hole toward the exhaust hole along the flow path PT in the duct 71.

As illustrated in FIGS. 3 and 4, the heat sink 8 includes first to third heat spreaders 811 to 813, first and second heat dissipation portions 821 and 822, and first to third heat pipes 831 to 833.

As illustrated in FIGS. 3 and 4, the first heat spreader 811 has a flat plate shape thermally connected to a back surface of the red light source 611, and is a heat receiving portion that receives heat generated in the red light source 611.

As illustrated in FIGS. 3 and 4, the second heat spreader 812 has a flat plate shape thermally connected to a back surface of the green light source 612, and is a heat receiving portion that receives heat generated in the green light source 612.

As illustrated in FIGS. 3 and 4, the third heat spreader 813 has a flat plate shape thermally connected to a back surface of the blue light source 613, and is a heat receiving portion that receives heat generated in the blue light source 613.

The first to third heat spreaders 811 to 813 are configured as independent parts. However, the embodiment is not limited to such a configuration, and the first to third heat spreaders 811 to 813 may be implemented by one part shared with the red, green, and blue light sources 611 to 613.

The first heat dissipation portion 821 is disposed in the duct 71 and includes a plurality of plate-shaped fins whose front and back surfaces are along the flow path PT (along an X-Z plane). That is, the first heat dissipation portion 821 is disposed on a lower side (a −Z-axis direction side) of the red, green, and blue light sources 611 to 613, the first to fourth lenses 621 to 624, and the first to third dichroic mirrors 631 to 633. Then, the first heat dissipation portion 821 dissipates heat generated by the red, green, and blue light sources 611 to 613 to the air flowing along the flow path PT.

The second heat dissipation portion 822 is disposed in the duct 71 and includes a plurality of plate-shaped fins whose front and back surfaces are along the flow path PT (along the X-Z plane). That is, the second heat dissipation portion 822 is disposed on a lower side (on a −Z-axis direction side) of the red, green, and blue light sources 611 to 613, the first to fourth lenses 621 to 624, and the first to third dichroic mirrors 631 to 633. Then, the second heat dissipation portion 822 dissipates heat generated by the green and blue light sources 612 and 613 to the air flowing along the flow path PT.

That is, the first and second heat dissipation portions 821 and 822 are configured as independent parts.

More specifically, as illustrated in FIGS. 3 and 4, lengths of the plurality of fins included in the first heat dissipation portion 821 are larger than lengths of the plurality of fins included in the second heat dissipation portion 822. In addition, as illustrated in FIG. 3, the first heat dissipation portion 821 is disposed at a position closer to the disposition positions of the red, green, and blue light sources 611 to 613 than the second heat dissipation portion 822 is (a position on a −Y-axis direction side of the second heat dissipation portion 822). In the first and second heat dissipation portions 821 and 822, a distal end of the second heat dissipation portion 822 positioned upstream (+X-axis direction side) on the flow path PT is positioned downstream (−X-axis direction side) of the flow path PT with respect to a distal end of the first heat dissipation portion 821 positioned upstream (+X-axis direction side) on the flow path PT. That is, in the first and second heat dissipation portions 821 and 822, the first heat dissipation portion 821 protrudes toward upstream (+X-axis direction side) on the flow path PT such that the first and second heat dissipation portions 821 and 822 are disposed in a stepped shape as a whole. As a result, in the air flowing through the flow path PT, air not passing through the first heat dissipation portion 821 flows through the second heat dissipation portion 822.

Here, an interval between the plurality of fins included in the second heat dissipation portion 822 is smaller than an interval between the plurality of fins included in the first heat dissipation portion 821.

As illustrated in FIG. 4, one end of the first heat pipe 831 is thermally connected to the first heat spreader 811, extends downward (toward the −Z-axis direction) from the one end, is bent by approximately 90°, and extends in a +Y-axis direction. In addition, the first heat pipe 831 is thermally connected to the first heat dissipation portion 821 in a state where the other end side portion of the first heat pipe 831 penetrates through each of the plurality of fins included in the first heat dissipation portion 821. Then, the first heat pipe 831 transfers heat of the first heat spreader 811 (the heat of the red light source 611) from one end toward the other end.

As illustrated in FIG. 4, one end of the second heat pipe 832 is thermally connected to the second heat spreader 812, extends downward (toward the −Z-axis direction) from the one end, is bent by approximately 90°, and extends in the +Y-axis direction. In addition, the second heat pipe 832 is thermally connected to the first and second heat dissipation portions 821 and 822 in a state where the other end side portion of the second heat pipe 832 penetrates through each of the plurality of fins included in the first heat dissipation portion 821 and the plurality of fins included in the second heat dissipation portion 822. Then, the second heat pipe 832 transfers heat of the second heat spreader 812 (the heat of the green light source 612) from one end toward the other end.

As illustrated in FIG. 4, one end of the third heat pipe 833 is thermally connected to the third heat spreader 813, extends downward (toward the −Z-axis direction) from the one end, is bent by approximately 90°, and extends in the +Y-axis direction. In addition, the third heat pipe 833 is thermally connected to the first and second heat dissipation portions 821 and 822 in a state where the other end side portion of the third heat pipe 833 penetrates through each of the plurality of fins included in the first heat dissipation portion 821 and the plurality of fins included in the second heat dissipation portion 822. The third heat pipe 833 transfers heat of the third heat spreader 813 (the heat of the blue light source 613) from one end toward the other end.

Here, an allowable thermal resistance for the heat sink in the red light source 611 calculated from a difference between the maximum junction temperature (first temperature) and an ambient temperature and a heat generation amount of the red light source 611 is higher than an allowable thermal resistance for the heat sink in the green light source 612 calculated from a difference between the maximum junction temperature (third temperature) and an ambient temperature and a heat generation amount of the green light source 612. More specifically, the allowable thermal resistance is a value obtained by dividing the difference [° C.] between the maximum junction temperature and the ambient temperature by the heat generation amount [W].

According to the first embodiment described above, the following effects are obtained.

In the light source device 6 according to the first embodiment, the heat sink 8 includes the first heat dissipation portion 821 that is disposed on the flow path PT of the air and dissipates the heat of the red and green light sources 611 and 612 to the air, and the second heat dissipation portion 822 that is disposed on the flow path PT and dissipates the heat of the green light source 612 to the air. Further, the allowable thermal resistance for the heat sink in the red light source 611 calculated from the difference between the maximum junction temperature (first temperature) and the ambient temperature and the heat generation amount of the red light source 611 is higher than the allowable thermal resistance for the heat sink in the green light source 612 calculated from the difference between the maximum junction temperature (third temperature) and the ambient temperature and the heat generation amount of the green light source 612. Further, in the first and second heat dissipation portions 821 and 822, the first heat dissipation portion 821 protrudes toward upstream (+X-axis direction side) on the flow path PT such that the first and second heat dissipation portions 821 and 822 are disposed in a stepped shape as a whole. As a result, in the air flowing through the flow path PT, air not passing through the first heat dissipation portion 821 flows through the second heat dissipation portion 822. Therefore, the heat of the green light source 612 whose heat generation amount is large can be sufficiently dissipated, and the temperature of the red light source 611 adjacent to the green light source 612 does not rise. That is, the red light source 611 can maintain an appropriate temperature, and light emission efficiency of the red light source 611 can be favorably maintained.

Therefore, with the light source device 6 according to the first embodiment, it is possible to efficiently dissipate the heat of the red and green light sources 611 and 612 while using the first heat dissipation portion 821 shared with the red and green light sources 611 and 612.

In particular, the interval between the plurality of fins included in the second heat dissipation portion 822 is smaller than the interval between the plurality of fins included in the first heat dissipation portion 821. Therefore, a flow velocity of air flowing between the plurality of fins included in the second heat dissipation portion 822 can be increased, and the temperature of the green light source 612 can be preferentially lowered. As a result, the temperature of the red light source 611 adjacent to the green light source 612 can also be lowered.

Modification 1-1

Figure 5:
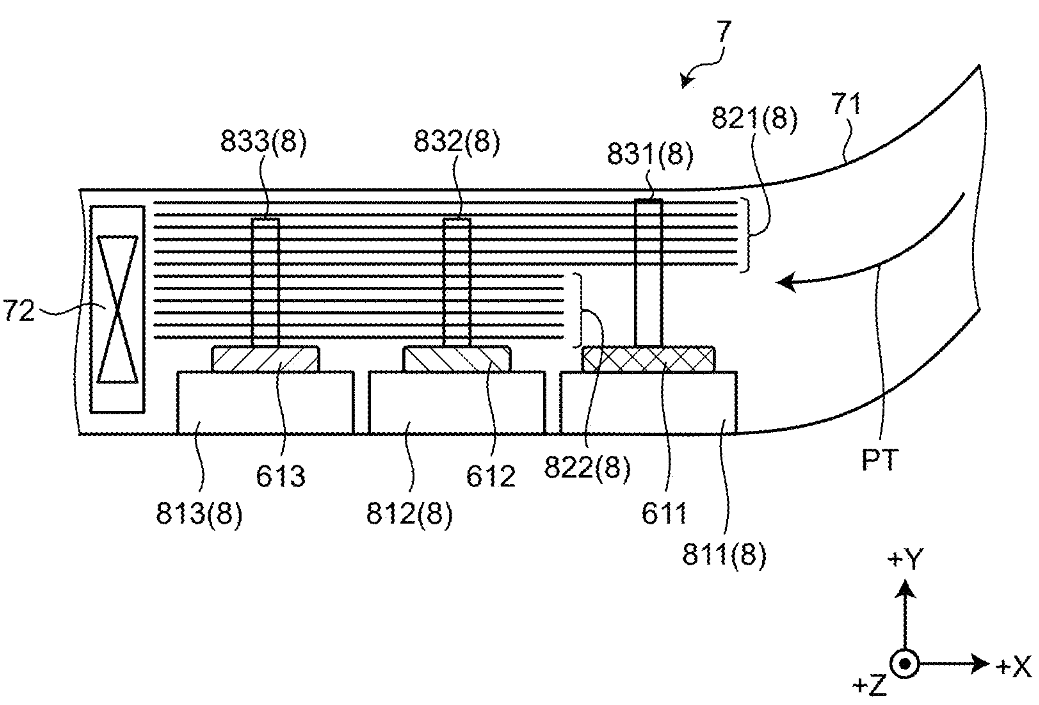
FIG. 5 is a view for describing Modification 1-1 of the first embodiment.
Figure 6:
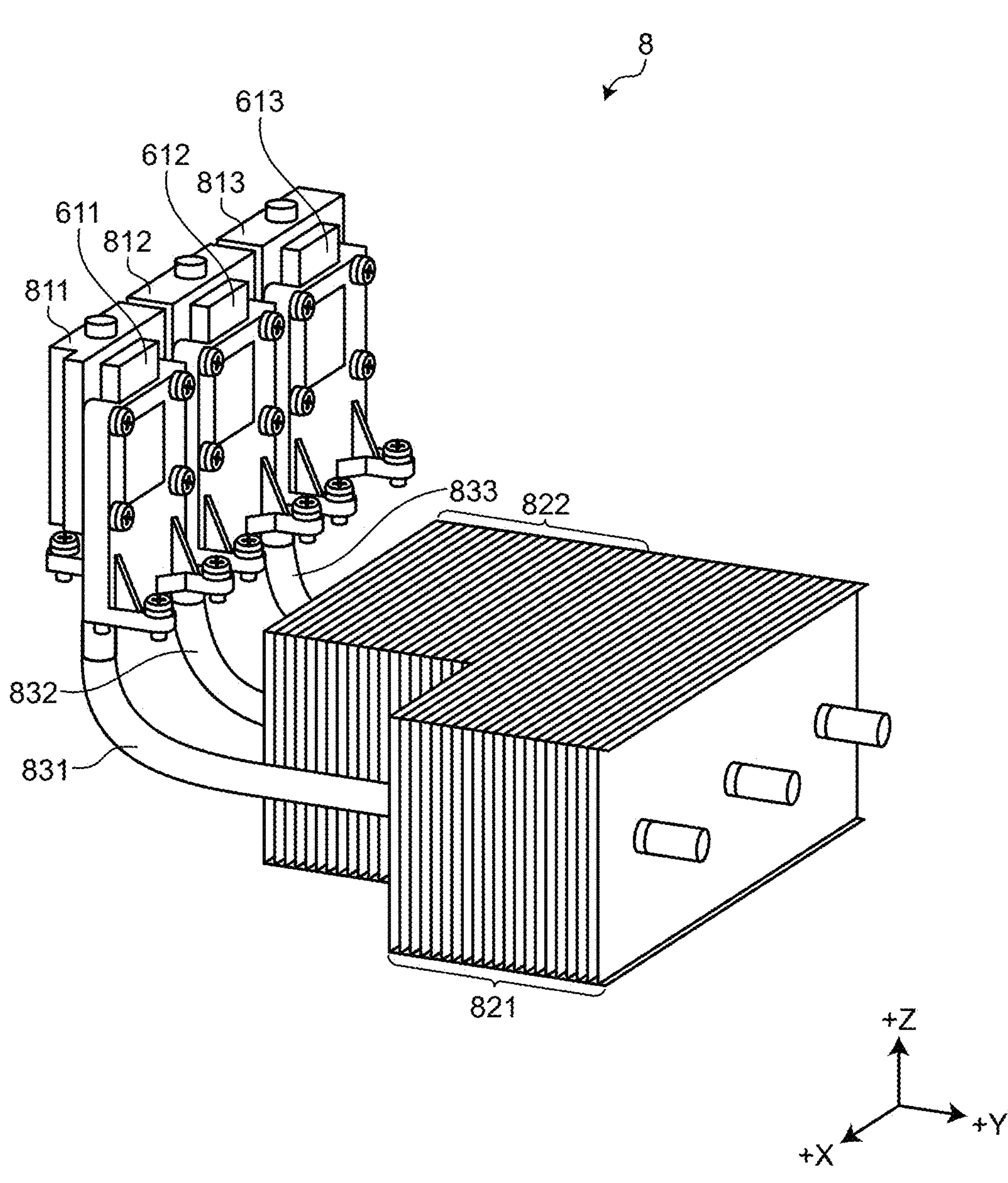
FIG. 6 is a view for describing Modification 1-1 of the first embodiment.

FIGS. 5 and 6 are views for describing Modification 1-1 of the first embodiment. Specifically, FIG. 5 is a view corresponding to FIG. 3. FIG. 6 is a view corresponding to FIG. 4.

In the first embodiment described above, the first heat dissipation portion 821 is disposed at a position closer to the disposition positions of the red, green, and blue light sources 611 to 613 than the second heat dissipation portion 822 is (a position on a −Y-axis side of the second heat dissipation portion 822), but the embodiment is not limited thereto. As in Modification 1-1 illustrated in FIGS. 5 and 6, the second heat dissipation portion 822 may be disposed at a position closer to the disposition positions of the red, green, and blue light sources 611 to 613 than the first heat dissipation portion 821 is (a position on a −Y-axis side of the first heat dissipation portion 821).

According to Modification 1-1 described above, in addition to the same effect as that of the first embodiment described above, the following effects are obtained.

Unlike the configuration in the first embodiment described above, in Modification 1-1, the second heat dissipation portion 822 is disposed at a position closer to the disposition positions of the red, green, and blue light sources 611 to 613 than the first heat dissipation portion 821 is. Therefore, it is possible to preferentially cool the green light source 612.

Second Embodiment

Next, a second embodiment will be described.

In the following description, the same components as those in the first embodiment will be designated by the same reference signs, and a detailed description thereof will be omitted or simplified.

Figure 7:
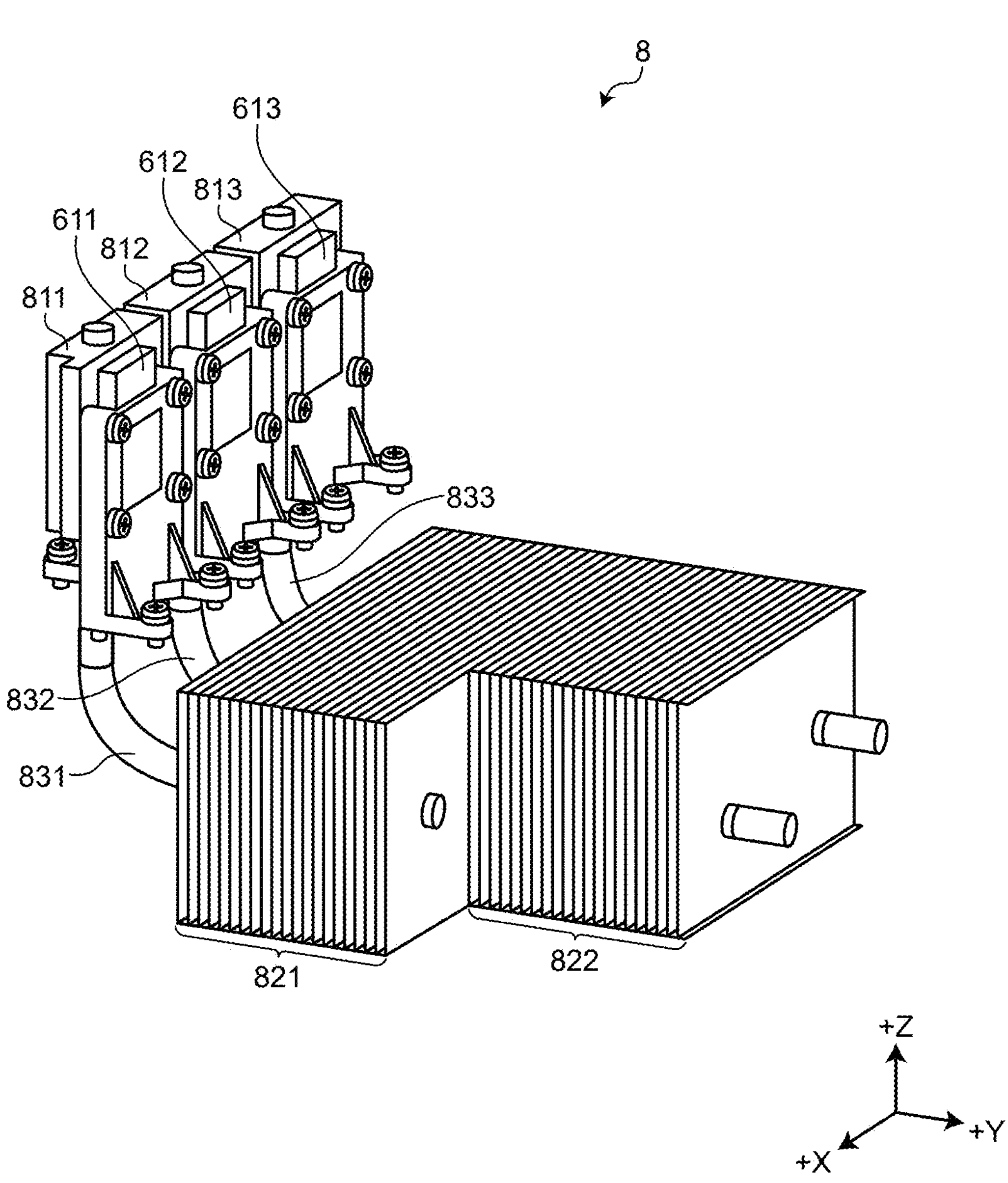
FIG. 7 is a view for describing a configuration of a cooling unit according to a second embodiment.
Figure 8:
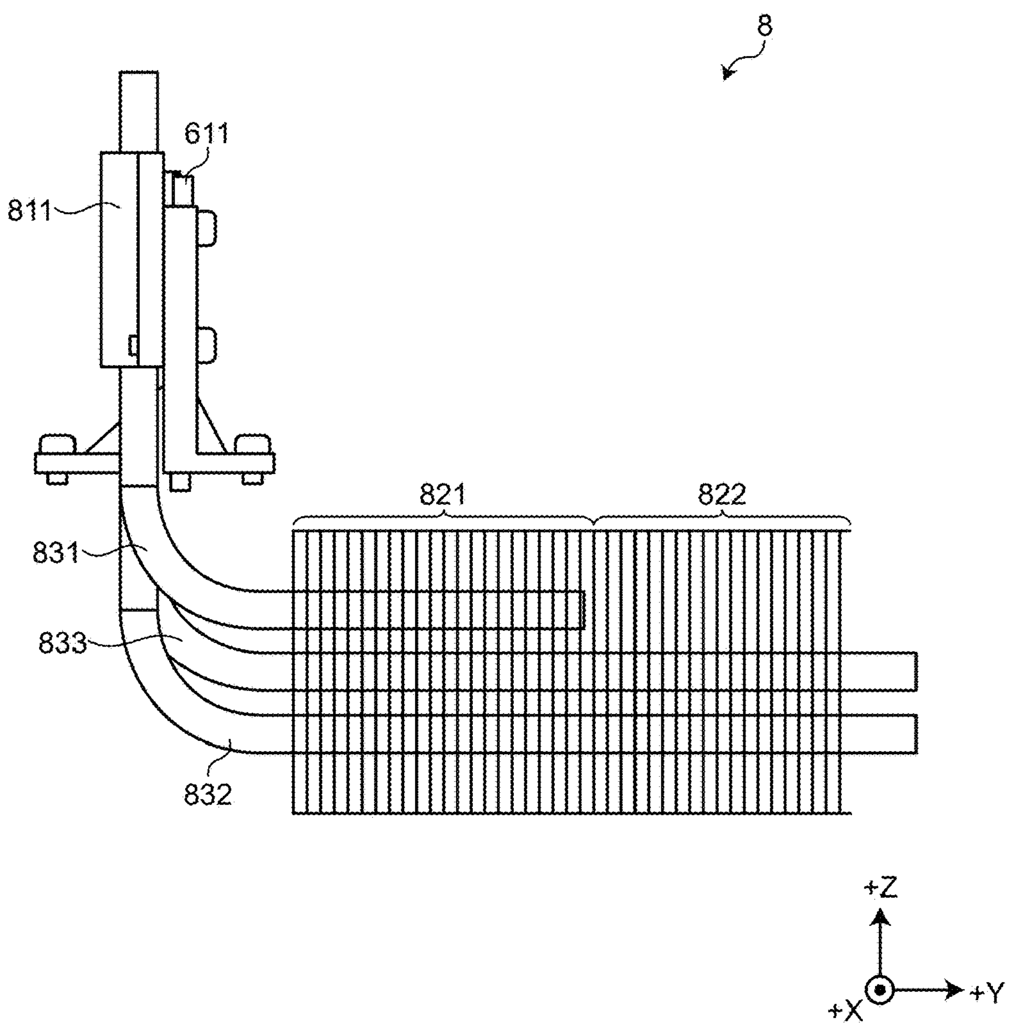
FIG. 8 is a view for describing a configuration of the cooling unit according to the second embodiment.
Figure 9:
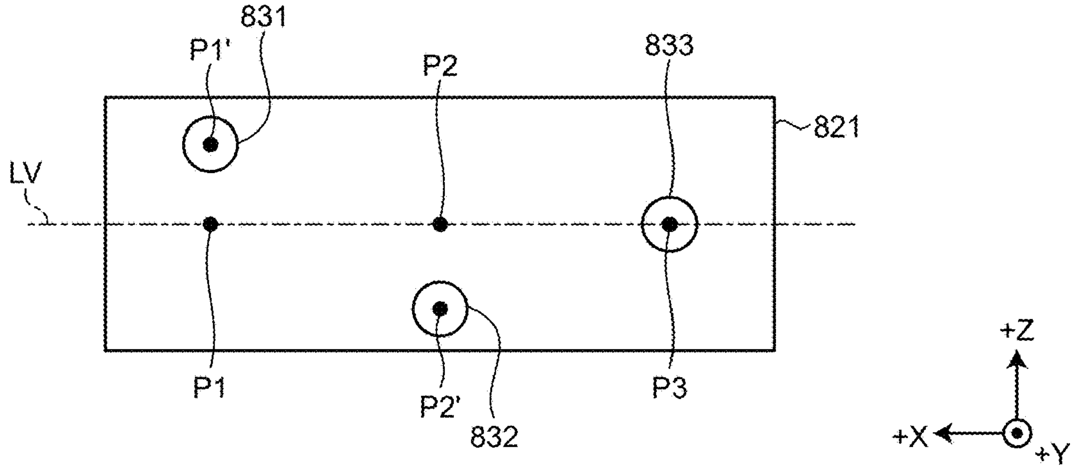
FIG. 9 is a view for describing a configuration of the cooling unit according to the second embodiment.

FIGS. 7 to 9 are views for describing a configuration of a heat sink 8 according to the second embodiment. Specifically, FIG. 7 is a view corresponding to FIG. 4. FIG. 8 is a view of the heat sink 8 when viewed from a +X-axis direction side. FIG. 9 is a view of the heat sink 8 when viewed from a +Y-axis direction side. In FIG. 9, a second heat dissipation portion 822 is omitted for convenience of description.

In the second embodiment, a configuration of the heat sink 8 is changed from that of the first embodiment described above. More specifically, in the heat sink 8 according to the first embodiment described above, first to third heat pipes 831 to 833 are disposed at first to third positions P1 to P3 on a virtual line LV along an X-axis direction orthogonal to a flow path PT in a first heat dissipation portion 821 as illustrated in FIG. 9. That is, height positions of the first to third positions P1 to P3 are all the same. The X-axis direction corresponds to a first direction. On the other hand, in the heat sink 8 according to the second embodiment, first and second heat pipes 831 and 832 are disposed at first and second positions P1' and P2' derived by shifting the first and second positions P1 and P2 toward opposite sides in a Z-axis direction in the first heat dissipation portion 821. More specifically, the height position of the first position P1' is higher than the height position of the second position P2'. The Z-axis direction corresponds to a second direction. The second heat pipe 832 is disposed at the third position P3 in the first heat dissipation portion 821 similarly to the first embodiment described above.

According to the second embodiment described above, in addition to the same effect as that of the first embodiment described above, the following effects are obtained.

In a light source device 6 according to the second embodiment, the first and second heat pipes 831 and 832 are disposed at the first and second positions P1' and P2' derived by shifting the first and second positions P1 and P2 toward opposite sides in the Z-axis direction in the first heat dissipation portion 821. Therefore, it is possible to achieve a structure in which air heated by the first heat dissipation portion 821 (red light source 611) connected to the first heat pipe 831 upstream on the flow path PT is hardly introduced into the second heat pipe 832 disposed downstream on the flow path PT. That is, a structure in which a temperature of a green light source 612 is easily lowered is implemented, and a temperature of the red light source 611 adjacent to the green light source 612 can also be lowered.

Modification 2-1

Figure 10:
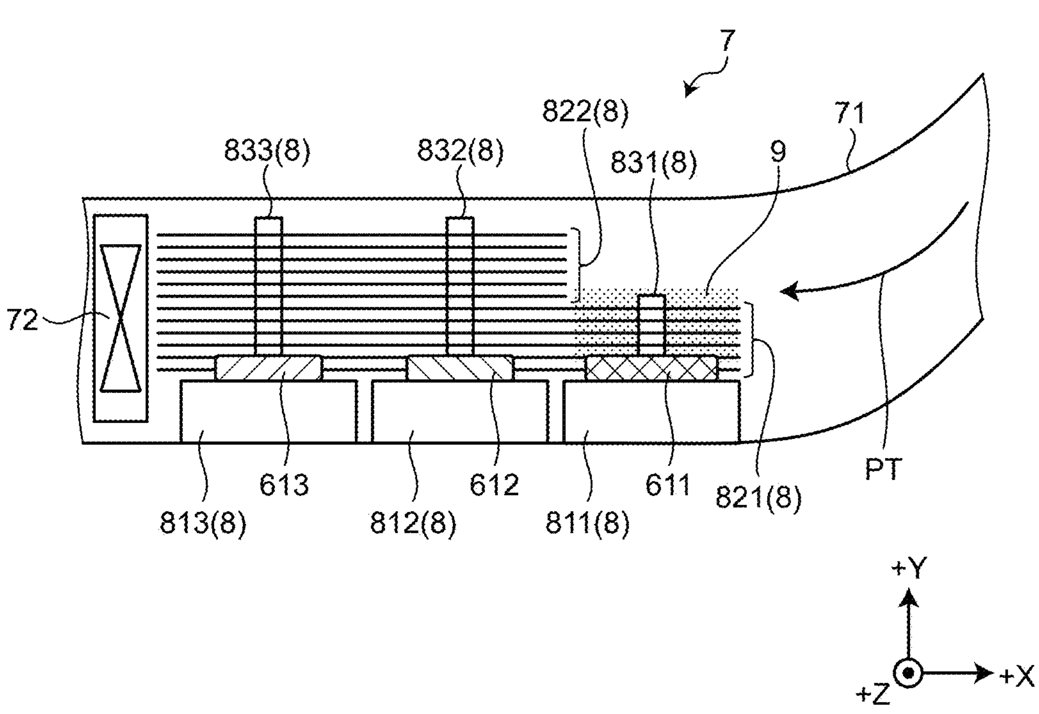
FIG. 10 is a view for describing Modification 2-1 of the second embodiment.
Figure 11:
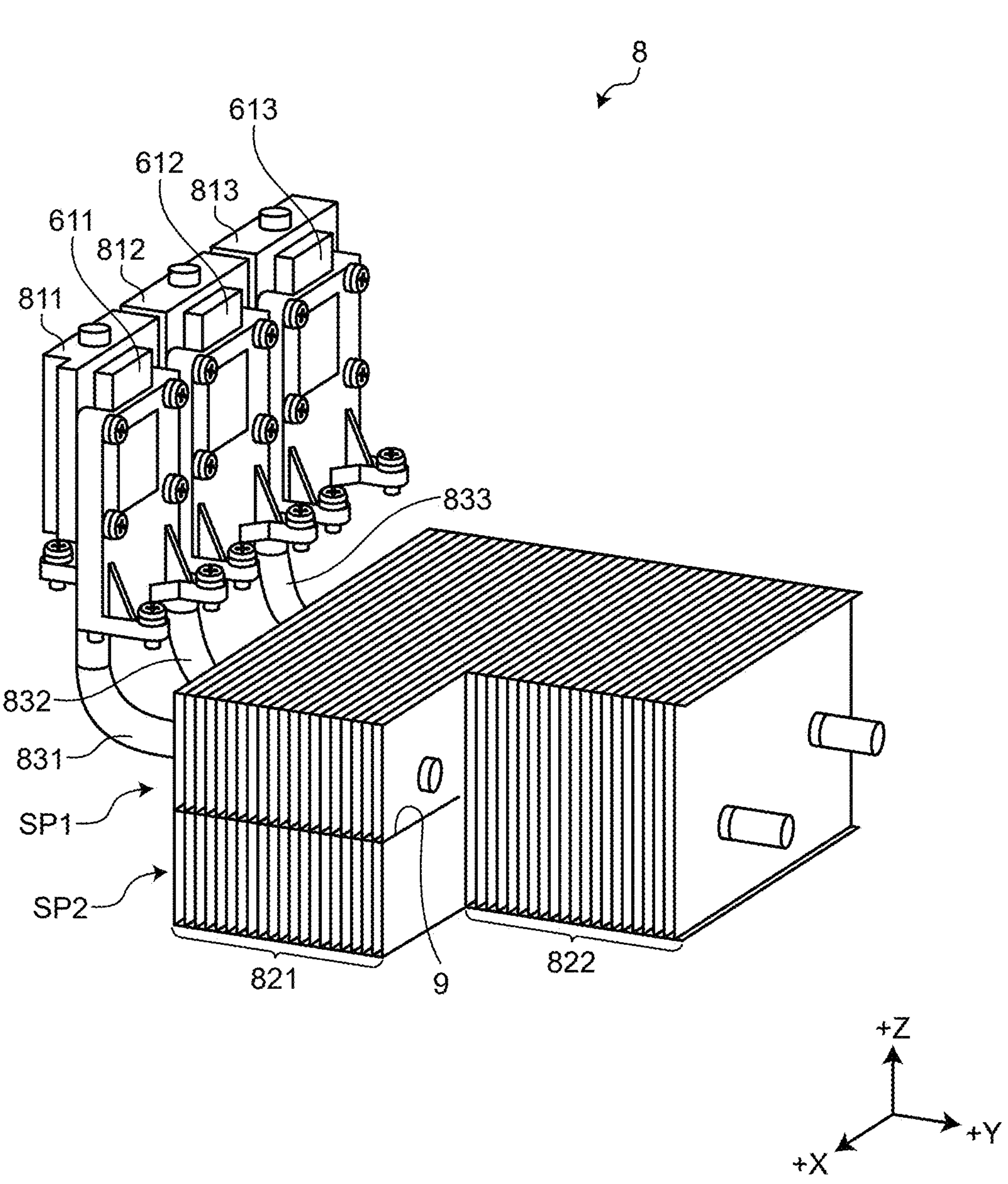
FIG. 11 is a view for describing Modification 2-1 of the second embodiment.

FIGS. 10 and 11 are views for describing Modification 2-1 of the second embodiment. Specifically, FIG. 10 is a view corresponding to FIG. 3, and is a plan view illustrating an overall configuration of a cooling unit 7 according to Modification 2-1. FIG. 11 is a view corresponding to FIG. 7.

In the second embodiment described above, a separator 9 may be adopted as in Modification 2-1 illustrated in FIGS. 10 and 11.

The separator 9 has a comb-tooth shape, and is disposed in a state of being inserted into a portion of the first heat dissipation portion 821 that protrudes from the second heat dissipation portion 822 toward upstream on the flow path PT as illustrated in FIGS. 10 and 11. The separator 9 causes air flowing through the flow path PT to separately flow into a first space SP1 (FIG. 11) on a side of the first heat pipe 831 and a second space SP2 (FIG. 11) on a side of the second heat pipe 832 in a Z axis direction.

According to Modification 2-1 described above, in addition to the same effect as that of the second embodiment described above, the following effects are obtained.

In Modification 2-1, the separator 9 described above is adopted. Therefore, a larger amount of fresh air can be introduced into the second heat pipe 832 disposed downstream on the flow path PT. That is, a structure in which the temperature of the green light source 612 is easily lowered is implemented, and the temperature of the red light source 611 adjacent to the green light source 612 can also be lowered.

Modification 2-2

Figure 12:
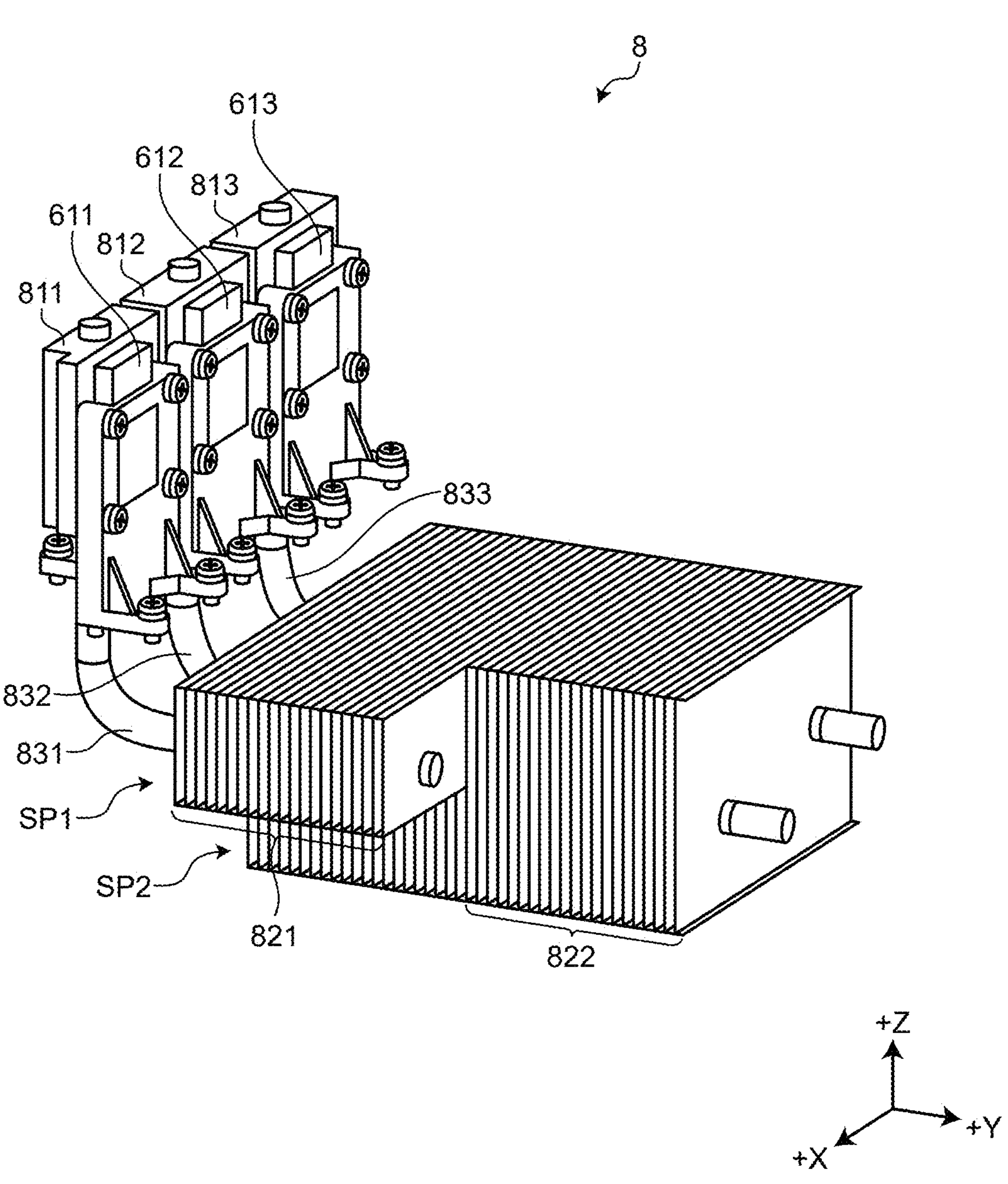
FIG. 12 is a view for describing Modification 2-2 of the second embodiment.

FIG. 12 is a view for describing Modification 2-2 of the second embodiment. Specifically, FIG. 12 is a view corresponding to FIG. 11.

In the first heat dissipation portion 821 according to Modification 2-1 described above, a configuration in which a portion on a second space SP2 side separated by the separator 9 is omitted in a portion protruding from the second heat dissipation portion 822 upstream (+X-axis direction side) on the flow path PT as in Modification 2-2 illustrated in FIG. 12 may be adopted. The separator 9 may be provided or does not have to be provided.

Even in a case where the configuration of Modification 2-2 described above is adopted, the same effects as those of Modification 2-1 described above are obtained.

Modification 2-3

Figure 13:
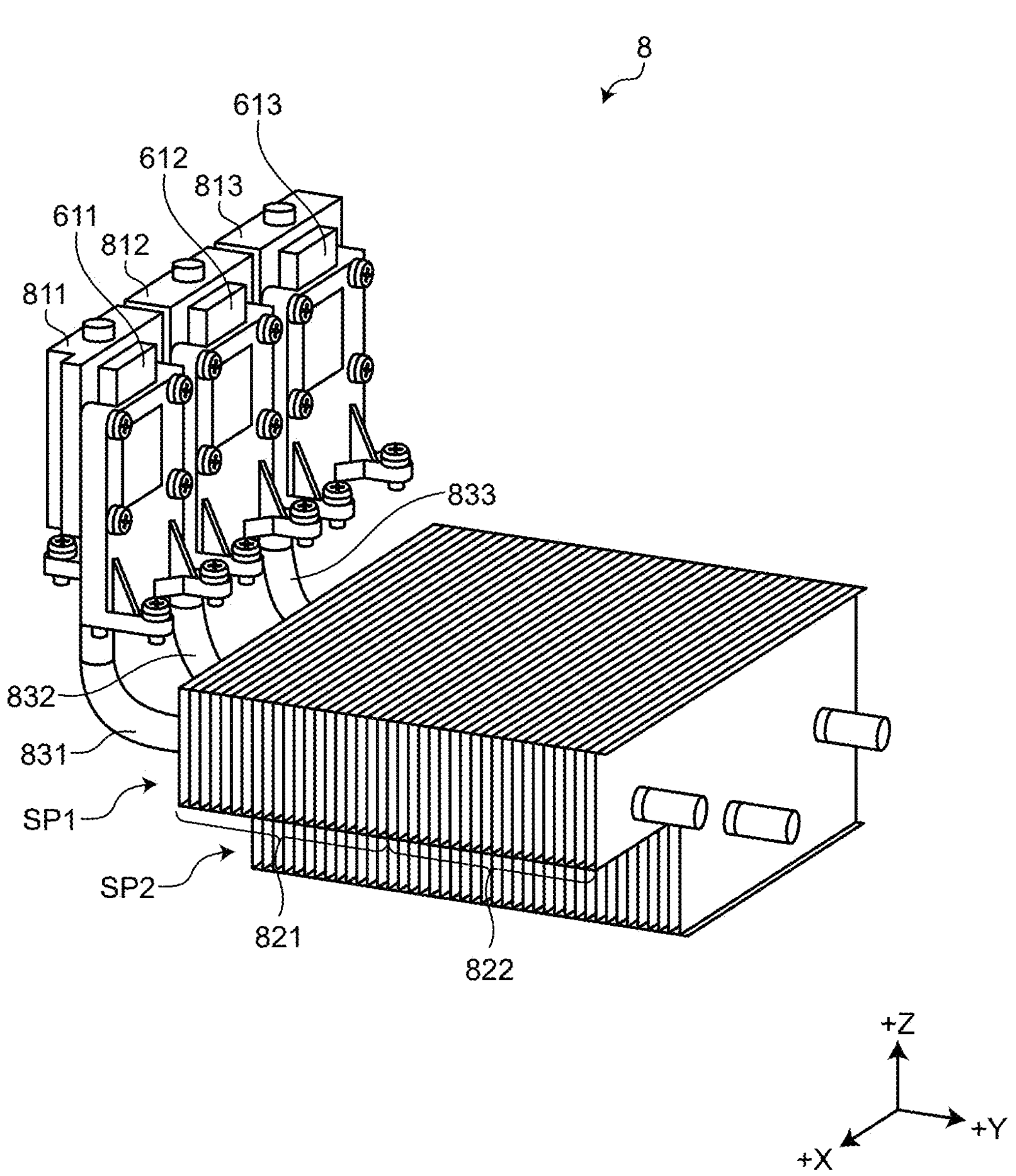
FIG. 13 is a view for describing Modification 2-3 of the second embodiment.

FIG. 13 is a view for describing Modification 2-3 of the second embodiment. Specifically, FIG. 13 is a view corresponding to FIG. 12.

As in Modification 2-3 illustrated in FIG. 13, a plurality of fins included in the second heat dissipation portion 822 according to Modification 2-2 described above may be changed so as to have the same shape as that of a plurality of fins included in the first heat dissipation portion 821 according to Modification 2-2 described above.

Even in a case where the configuration of Modification 2-3 described above is adopted, the same effects as those of Modification 2-2 described above are obtained.

Other Embodiments

Although the embodiments for carrying out the present invention have been described so far, the present invention should not be limited only to the first and second embodiments and Modifications 1-1 and 2-1 to 2-3 described above.

In the first and second embodiments and Modifications 1-1 and 2-1 to 2-3 described above, the light source device is mounted on the endoscope system 1 using a flexible endoscope, but the embodiment is not limited thereto, and the light source device may be mounted on an endoscope system using a rigid endoscope. In addition, the light source device may be mounted on an observation system using a surgical microscope that enlarges and captures an image of a predetermined visual field region inside a subject (inside a living body) or on a surface of the subject (a surface of the living body).

In the first and second embodiments and Modifications 1-1 and 2-1 to 2-3 described above, the first light emitting element is the red light source 611, and the second light emitting element is the green light source 612, but the embodiment is not limited thereto. Wavelength bands of rays of light emitted from the first and second light emitting elements are not limited to the wavelength bands described in the first and second embodiments and Modification 1-1 and 2-1 to 2-3, and may be other wavelength bands.

In the first and second embodiments and Modifications 1-1 and 2-1 to 2-3 described above, the first and second heat dissipation portions are not limited to those including a plurality of plate-shaped fins, and may include a plurality of protruding fins or may have a block shape.

In the first and second embodiments and Modifications 1-1 and 2-1 to 2-3 described above, Modifications 3-1 to 3-3 described below may be adopted.

Modification 3-1

Hereinafter, for convenience of description, the red, green, and blue light sources 611 to 613 will be collectively referred to as a light emitting element 61. The first to third heat spreaders 811 to 813 are collectively referred to as a heat spreader 81.

Figure 14:
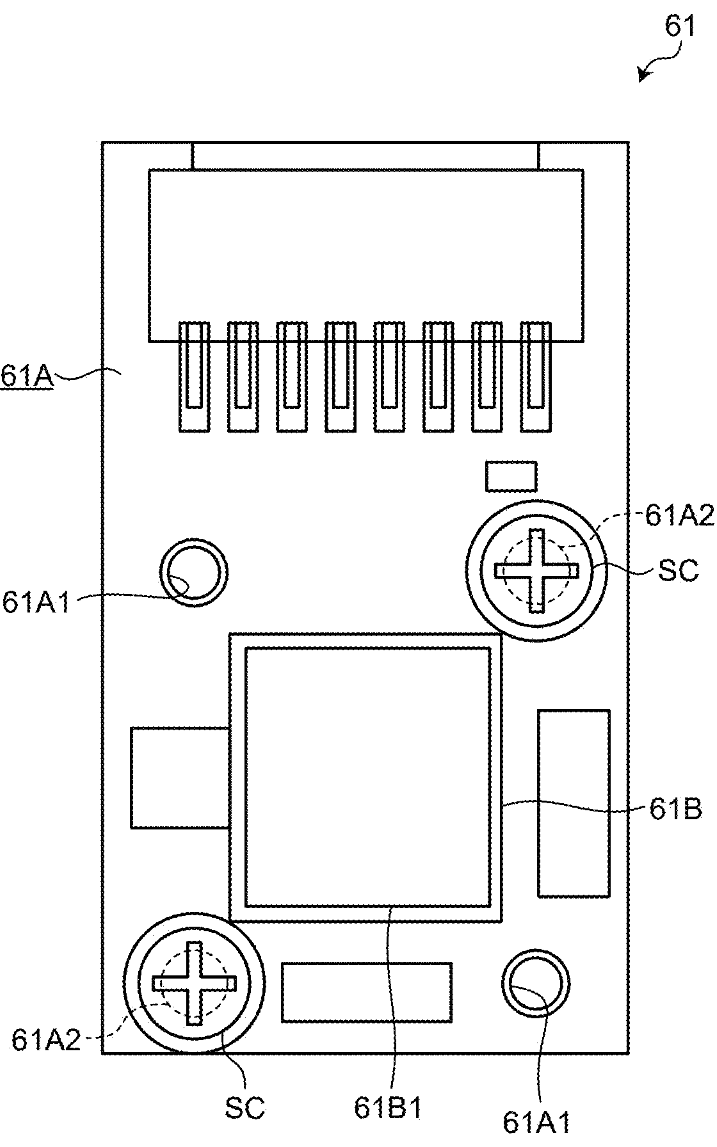
FIG. 14 is a view for describing Modification 3-1 of the first and second embodiments and Modifications 1-1 and 2-1 to 2-3.
Figure 15:
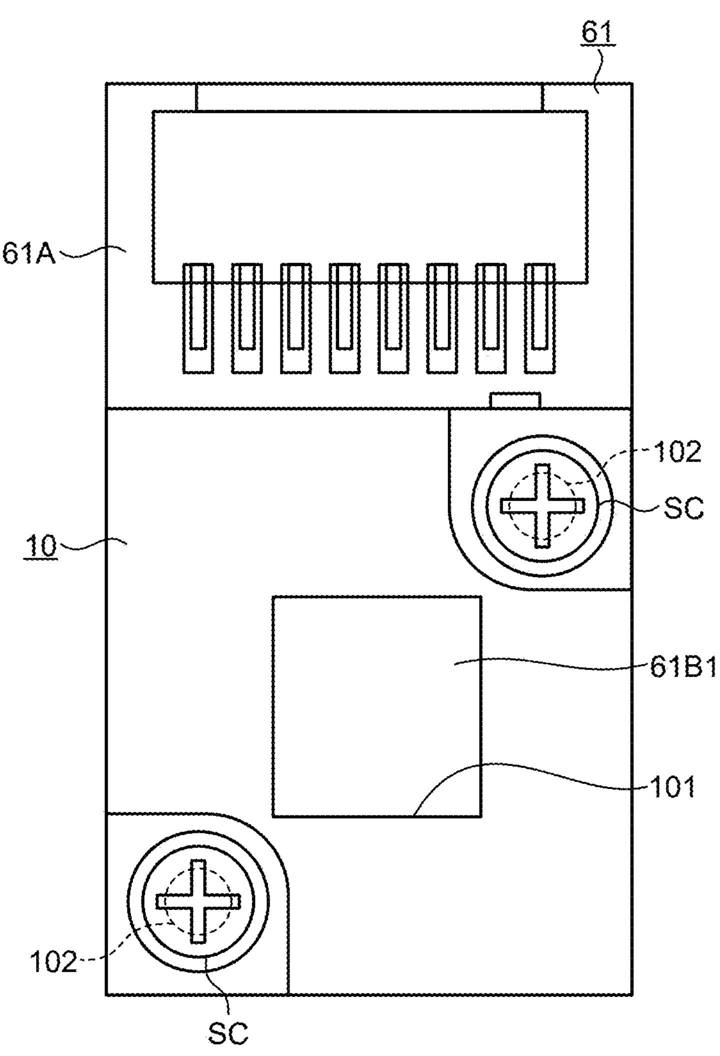
FIG. 15 is a view for describing Modification 3-1 of the first and second embodiments and Modifications 1-1 and 2-1 to 2-3.

FIGS. 14 and 15 are views for describing Modification 3-1 of the first and second embodiments and Modifications 1-1 and 2-1 to 2-3. Specifically, FIG. 14 is a view of the light emitting element 61 when viewed from the front (light emission side). FIG. 15 is a view of a structure for fixing the light emitting element 61 to the heat spreader 81 when viewed from the front.

In the first and second embodiments and Modifications 1-1 and 2-1 to 2-3 described above, the fixing structure of Modification 3-1 illustrated in FIG. 15 may be adopted as a structure for fixing the light emitting element 61 to the heat spreader 81.

Here, as illustrated in FIG. 14, the light emitting element 61 has a configuration in which a chip 61B having a light emitting surface 61B1 that emits light is mounted on a circuit board 61A. In the circuit board 61A, a pair of positioning holes 61A1 penetrating through front and back surfaces of the circuit board 61A are provided at two positions sandwiching the light emitting surface 61B1. In the circuit board 61A, a pair of attachment holes 61A2 penetrating through the front and back surfaces of the circuit board 61A are provided at two positions sandwiching the light emitting surface 61B1.

In Modification 3-1, as illustrated in FIG. 15, a frame portion 10 is used as the structure for fixing the light emitting element 61 to the heat spreader 81.

The frame portion 10 includes a plate body, and sandwiches the light emitting element 61 with the heat spreader 81. In the frame portion 10, as illustrated in FIG. 15, an aperture 101 which penetrates through the front and back surfaces and through which the light emitted from the light emitting surface 61B1 passes is provided at a position facing the light emitting surface 61B1. That is, the frame portion 10 has a hollow rectangular shape. Further, in the frame portion 10, insertion holes 102 which penetrate through the front and back surfaces and into which fixing portions SC such as screws are inserted are provided at positions facing the pair of attachment holes 61A2.

The frame portion 10 described above is preferably made of a resin having an insulating property and light resistance to ultraviolet rays. Examples of the resin include polyether ether ketone (PEEK), polycarbonate, and acryl.

Then, the light emitting element 61 is attached to the heat spreader 81 as described below.

First, the operator inserts a positioning pin (not illustrated) into each of the pair of positioning holes 61A1 in the light emitting element 61, and inserts the positioning pin into each of a pair of positioning holes (not illustrated) formed in the heat spreader 81. Thus, the light emitting element 61 is optically positioned.

Next, the operator places the frame portion 10 on a front side of the light emitting element 61, inserts the fixing portion SC into each of the pair of insertion holes 102 in the frame portion 10 and the pair of attachment holes 61A2 in the light emitting element 61, and fastens the fixing portion SC to the heat spreader 81. In this way, the light emitting element 61 is fixed to the heat spreader 81.

According to Modification 3-1 described above, in addition to the same effects as those of the first and second embodiments and Modifications 1-1 and 2-1 to 2-3, the following effects are obtained.

In Modification 3-1, the frame portion 10 described above is adopted. Therefore, a fastening force by the fixing portion SC can be dispersed by the frame portion 10, and the back surface of the light emitting element 61 can be uniformly pressed against the heat spreader 81. As a result, a contact thermal resistance between the light emitting element 61 and the heat spreader 81 can be reduced, and heat of the light emitting element 61 can be effectively dissipated to the heat spreader 81.

Note that a thermally conductive sheet such as a thermal interface material (TIM) may be interposed between the back surface of the light emitting element 61 and the heat spreader 81. The same applies to Modifications 3-2 and 3-3 described below.

Modification 3-2

Figure 16:
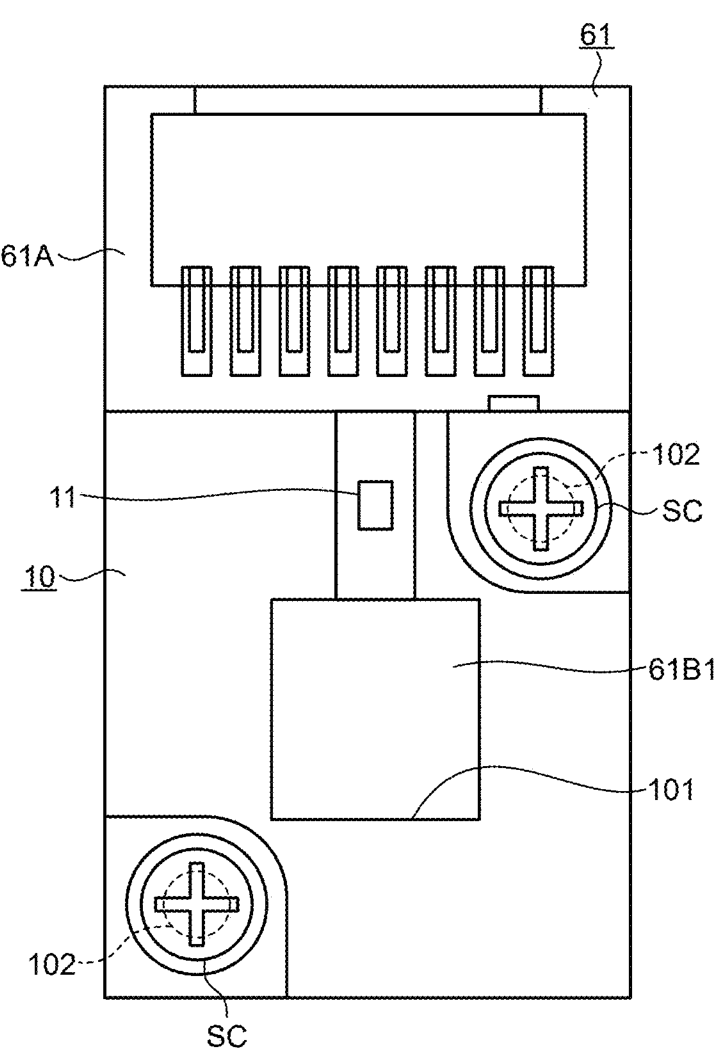
FIG. 16 is a view for describing Modification 3-2 of the first and second embodiments and Modifications 1-1 and 2-1 to 2-3.

FIG. 16 is a view for describing Modification 3-2 of the first and second embodiments and Modifications 1-1 and 2-1 to 2-3. Specifically, FIG. 16 is a view corresponding to FIG. 15.

In Modification 3-1 described above, in a case where a sensor 11 (FIG. 16) that detects a part of the light emitted from the light emitting surface 61B1 is attached to the light emitting element 61, the frame portion 10 according to Modification 3-2 illustrated in FIG. 16 may be adopted.

As illustrated in FIG. 16, in the frame portion 10 according to Modification 3-2, a part of an edge portion of the aperture 101 is cut out in order to avoid mechanical interference with the sensor 11. That is, the frame portion 10 according to Modification 3-2 has a U shape.

Even in a case where the configuration of the present Modification 3-2 described above is adopted, the same effects as those of Modification 3-1 described above are obtained.

Modification 3-3

Figure 17:
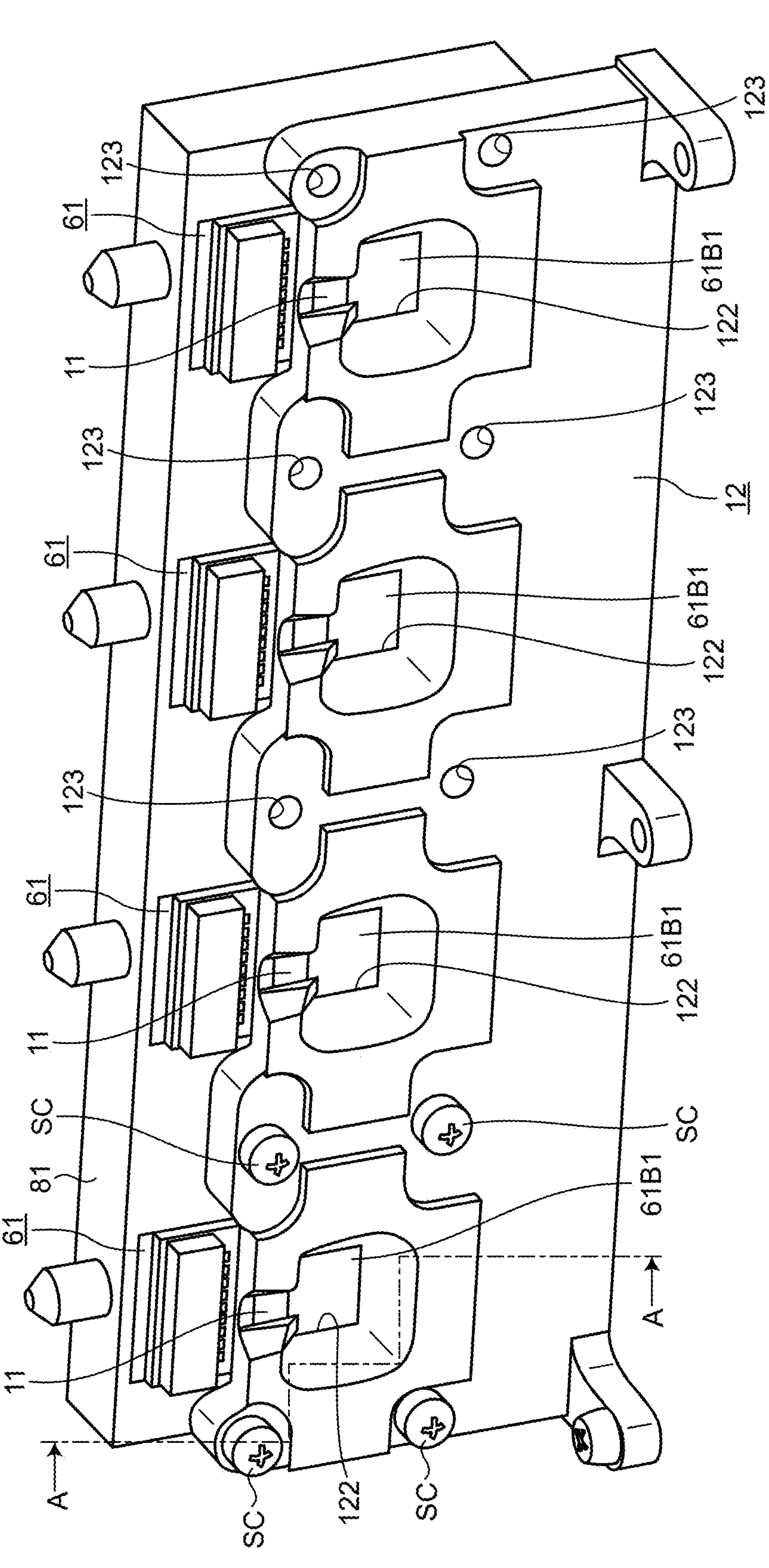
FIG. 17 is a view for describing Modification 3-3 of the first and second embodiments and Modifications 1-1 and 2-1 to 2-3.
Figure 18:
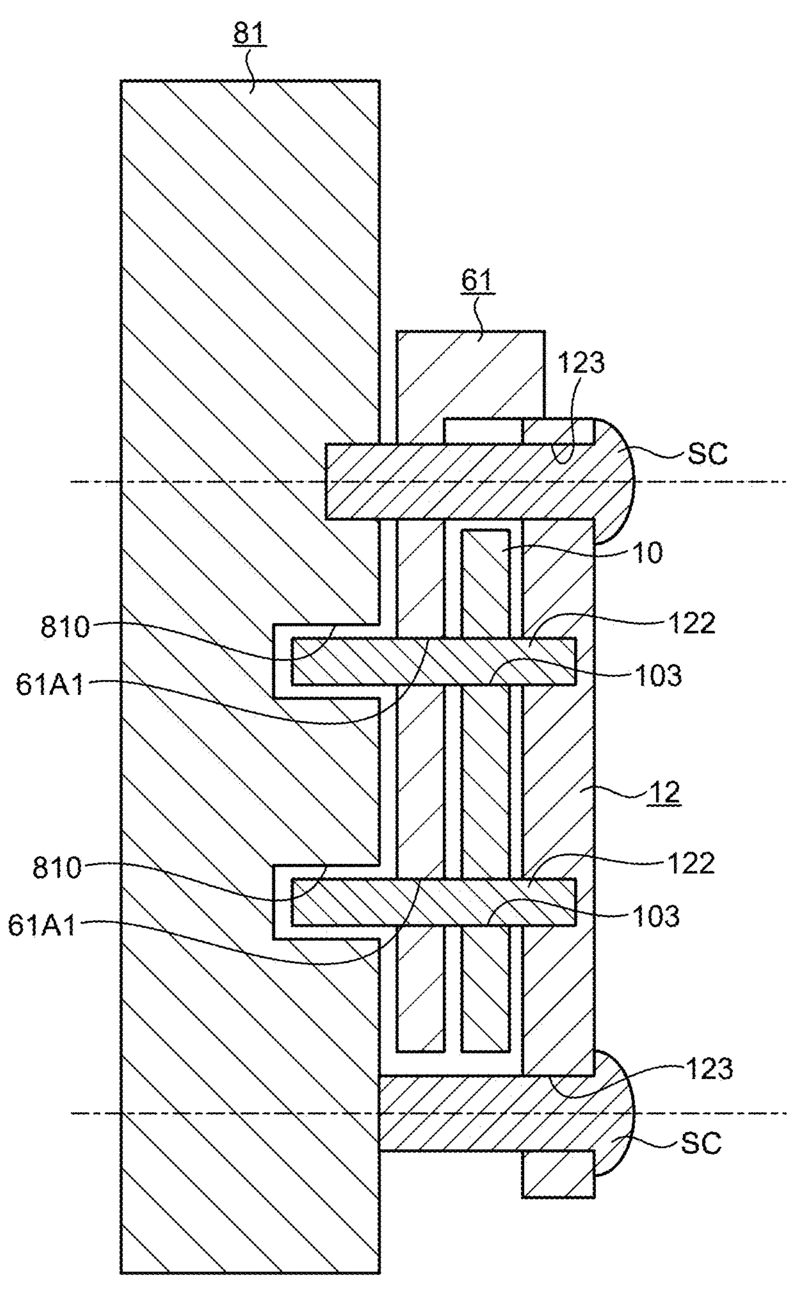
FIG. 18 is a view for describing Modification 3-3 of the first and second embodiments and Modifications 1-1 and 2-1 to 2-3.

FIGS. 17 and 18 are views for describing Modification 3-3 of the first and second embodiments and Modifications 1-1 and 2-1 to 2-3. Specifically, FIG. 17 is a perspective view of a structure for fixing the light emitting element 61 to the heat spreader 81 when viewed from the front. FIG. 17 illustrates a configuration using four light emitting elements 61 for convenience of description. In FIG. 17, the heat spreader 81 is shared with the four light emitting elements 61. FIG. 18 is a cross-sectional view taken along line A-A in FIG. 17.

In the first and second embodiments and Modifications 1-1 and 2-1 to 2-3 described above, the fixing structure according to Modification 3-3 illustrated in FIGS. 17 and 18 may be adopted as the structure for fixing the light emitting element 61 to the heat spreader 81.

In Modification 3-3, as illustrated in FIGS. 17 and 18, the frame portion 10 (FIG. 18) and a pressing portion 12 are used as the structure for fixing the light emitting element 61 to the heat spreader 81.

Here, as illustrated in FIG. 17, the sensor 11 is attached to the light emitting element 61 similarly to Modification 3-2 described above. The frame portion 10 according to Modification 3-3 has the same shape as that of Modification 3-2 described above. That is, the frame portion 10 according to Modification 3-3 is provided for each light emitting element 61.

The frame portion 10 according to Modification 3-3 is made of an elastomer having elasticity such as fluoro rubber.

Furthermore, in the frame portion 10 according to Modification 3-3, insertion holes 103 which penetrate through the front and back surfaces and through which positioning pins 121 are inserted are provided at positions facing the pair of positioning holes 61A1 (FIG. 18).

As illustrated in FIG. 17, the pressing portion 12 according to Modification 3-3 is shared with the four light emitting elements 61. The pressing portion 12 may be provided for each light emitting element 61.

The pressing portion 12 includes a plate body, and sandwiches the light emitting element 61 and the frame portion 10 with the heat spreader 81.

The positioning pins 121 protruding toward a back surface side as illustrated in FIG. 18 are provided at positions facing the pair of positioning holes 61A1 on a back surface of the pressing portion 12.

Further, in the pressing portion 12, as illustrated in FIG. 17, an aperture 122 which penetrates through the front and back surfaces and through which the light emitted from the light emitting surface 61B1 passes is provided at a position facing the light emitting surface 61B1. Here, similarly to the frame portion 10, in the pressing portion 12, a part of an edge portion of the aperture 122 is cut out in order to avoid mechanical interference with the sensor 11.

Further, in the pressing portion 12, as illustrated in FIG. 18, insertion holes 123 which penetrate through the front and back surfaces and through which the fixing portions SC are inserted are provided at positions avoiding the light emitting element 61 and the frame portion 10.

Then, the light emitting element 61 is attached to the heat spreader 81 as described below.

First, the operator inserts the positioning pin 121 into each of the pair of insertion holes 102 in the frame portion 10 and the pair of positioning holes 61A1 in the light emitting element 61, and inserts the positioning pin 121 into each of a pair of positioning holes 810 (FIG. 18) formed in the heat spreader 81. Thus, the light emitting element 61 is optically positioned.

Next, the operator inserts the fixing portion SC into each of the pair of insertion holes 123 in the pressing portion 12, and fastens the fixing portion SC to the heat spreader 81. In this way, the light emitting element 61 is fixed to the heat spreader 81.

Even in a case where the configuration of the present Modification 3-3 described above is adopted, the same effects as those of Modifications 3-1 and 3-2 described above are obtained.

With the light source device according to the disclosure, it is possible to efficiently dissipate heat of the plurality of light emitting elements while using the heat dissipation portion shared with the plurality of light emitting elements.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A light source device comprising:
a first light emitting element;
a second light emitting element disposed adjacent to the first light emitting element;
a heat sink disposed within a flow path of a fluid and comprising a first heat dissipation portion and a second heat dissipation portion configured to transfer heat generated by the first light emitting element and heat of the second light emitting element to the fluid
a first heat pipe thermally connecting the first light emitting element to only the first heat dissipation portion from among the first heat dissipation portion and the second heat dissipation portion; and
a second heat pipe thermally connecting the second light emitting element to the first heat dissipation portion and to the second heat dissipation portion.

2. The light source device according to claim 1, wherein a portion of the fluid that does not pass through the first heat dissipation portion flows through the second heat dissipation portion.

3. The light source device according to claim 1, wherein the first and second heat dissipation portions are disposed in a stepped shape as a whole such that a distal end of the second heat dissipation portion on an upstream side of the flow path is positioned downstream of the flow path with respect to a distal end of the first heat dissipation portion on the upstream side of the flow path.

4. The light source device according to claim 1, wherein the first light emitting element is disposed at a position upstream on the flow path with respect to the second light emitting element.

5. The light source device according to claim 1, wherein the first heat pipe and the second heat pipe are disposed at positions derived by shifting first and second positions on a virtual line along a first direction orthogonal to the flow path, toward opposite sides in a second direction orthogonal to the flow path and the first direction, in the first heat dissipation portion.

6. The light source device according to claim 5, wherein the first heat dissipation portion includes
a plurality of fins, and
a separator that causes the fluid to separately flow into a first space on a side of the first heat pipe and a second space on a side of the second heat pipe, in the second direction.

7. The light source device according to claim 1, wherein the first heat dissipation portion and the second heat dissipation portion are configured as independent parts.

8. The light source device according to claim 1, wherein the first heat dissipation portion and the second heat dissipation portion each include a plurality of fins.

9. The light source device according to claim 8, wherein an interval between the plurality of fins included in the second heat dissipation portion is smaller than an interval between the plurality of fins included in the first heat dissipation portion.

10. The light source device according to claim 1, wherein a maximum junction temperature of the first light emitting element is lower than a maximum junction temperature of the second light emitting element.

11. The light source device according to claim 1, wherein a heat generation amount of the second light emitting element is larger than a heat generation amount of the first light emitting element.

12. The light source device according to claim 1, wherein the first light emitting element is a light emitting element configured to emit red light.

13. The light source device according to claim 1, wherein the second light emitting element is a light emitting element configured to emit green light.

14. The light source device according to claim 1, wherein the first light emitting element and the second light emitting element are semiconductor light emitting elements.

15. A heat exchanger for a light source device comprising:

a heat sink configured to be disposed within a flow path of a fluid and comprising a first heat dissipation portion and a second heat dissipation portion that are adjacent to one another a first heat pipe thermally connected to only the first heat dissipation portion from among the first heat dissipation portion and the second heat dissipation portion and configured to be thermally connected to a first light emitting element; and a second heat pipe thermally connected to the first heat dissipation portion and the second heat dissipation portion and configured to be thermally connected to a second light emitting element.

16. A method of cooling a first light emitting element and a second light emitting element that is disposed adjacent to the first light emitting element which are both thermally connected to a heat sink that includes a first heat dissipation portion and a second heat dissipation portion disposed within a flow path of a fluid, the method comprising:

transferring heat from the first light emitting element to a first heat pipe;

transferring heat from the second light emitting element to a second heat pipe;

transferring heat from the first heat pipe to only the first heat dissipation portion from among the first heat dissipation portion and the second heat dissipation portion; and transferring heat from the second heat pipe to the first heat dissipation portion and to the second heat dissipation portion.

17. The light source device according to claim 15, wherein the first heat pipe and the second heat pipe are offset from one another in a direction perpendicular to the flow path.

18. The light source device according to claim 1, wherein:

a first allowable thermal resistance between the first light emitting element and the fluid isa difference between a maximum junction temperature and an ambient temperature divided by a heat generation amount of the first light emitting element;

a second allowable thermal resistance between the second light emitting element and the fluid is a difference between a maximum junction temperature and an ambient temperature divided by a heat generation amount of the second light emitting element; and the first allowable thermal resistance is greater than the second allowable thermal resistance.

19. The light source device according to claim 17, wherein the second heat pipe is longer than the first heat pipe.

20. The light source device according to claim 17, further comprising a third heat pipe thermally connected to the first heat dissipation portion and the second heat dissipation portion and configured to be thermally connected to a second light emitting element.

* * * * *